United States Patent [19]
Collins

[11] 3,998,221
[45] Dec. 21, 1976

[54] TABLE DRAPE ASSEMBLY AND METHOD
[75] Inventor: Robert F. Collins, Barrington, Ill.
[73] Assignee: The Kendall Company, Boston, Mass.
[22] Filed: Mar. 5, 1976
[21] Appl. No.: 664,136
[52] U.S. Cl. .......................... 128/132 D; 128/1 R; 108/90; 150/52 R
[51] Int. Cl.² .................................. A61F 13/00
[58] Field of Search .......... 128/132 D, 1 R, 303 R; 150/52 R; 108/90

[56] References Cited
UNITED STATES PATENTS

| | | | |
|---|---|---|---|
| 771,009 | 9/1904 | Guardia | 108/90 |
| 1,877,610 | 9/1932 | Steiner | 108/90 |
| 3,542,019 | 11/1970 | Gittins | 128/132 D |
| 3,738,405 | 6/1973 | Ericson | 128/132 D |
| 3,747,655 | 7/1973 | Hadtke | 150/52 R |
| 3,795,309 | 3/1974 | Link | 128/132 D |
| 3,856,005 | 12/1974 | Sislian | 128/132 D |

Primary Examiner—Lawrence W. Trapp
Attorney, Agent, or Firm—Powell L. Sprunger

[57] ABSTRACT

A drape assembly for a surgical equipment table comprising, a sterile set-up drape having a barrier panel which is unfolded from the assembly to cover a reference end edge of the table, and a sterile table drape. A first end portion of the table drape is unfolded from the assembly into a configuration extending past an edge of the table remote the reference edge. After placing sterile articles on the unfolded part of the table drape and positioning the table adjacent a patient, a second end portion of the table drape may be unfolded into a configuration covering the barrier panel.

24 Claims, 24 Drawing Figures

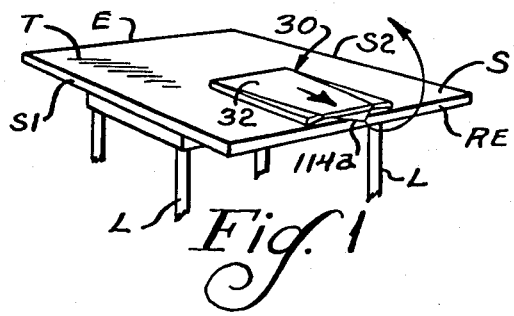
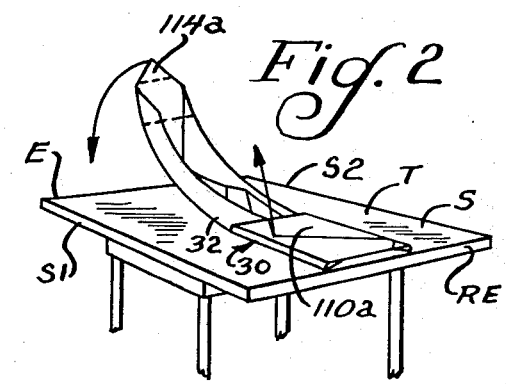
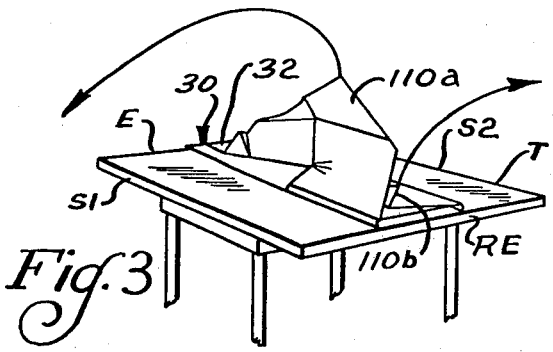
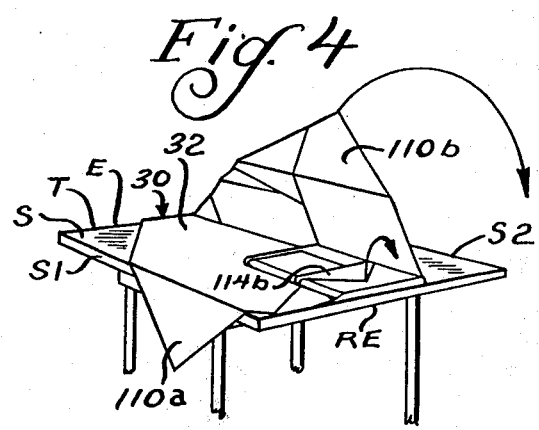
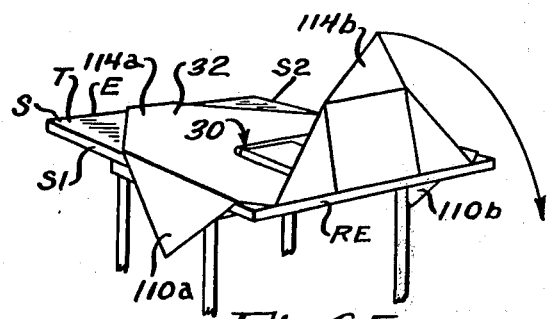
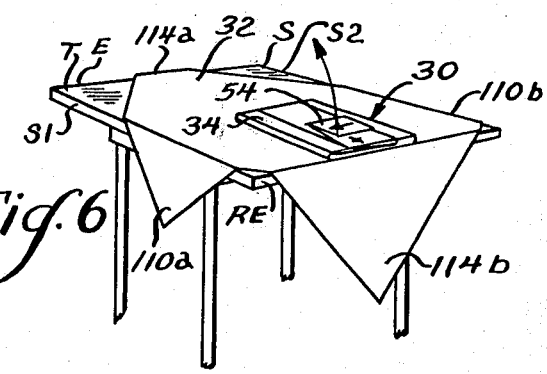
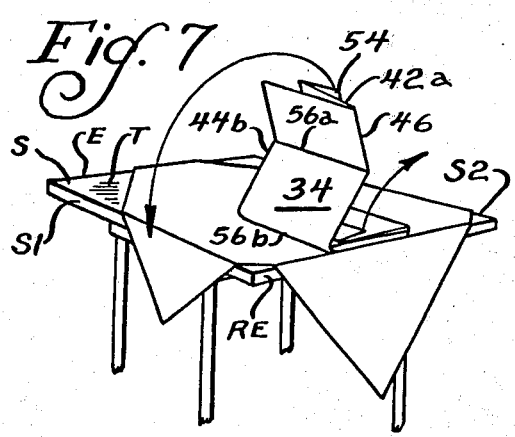
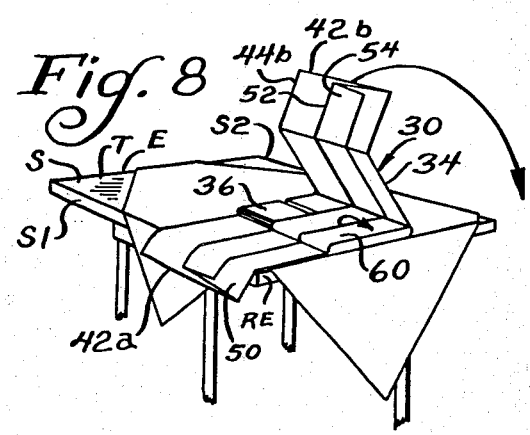

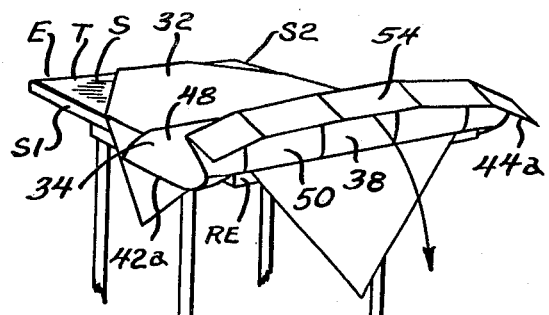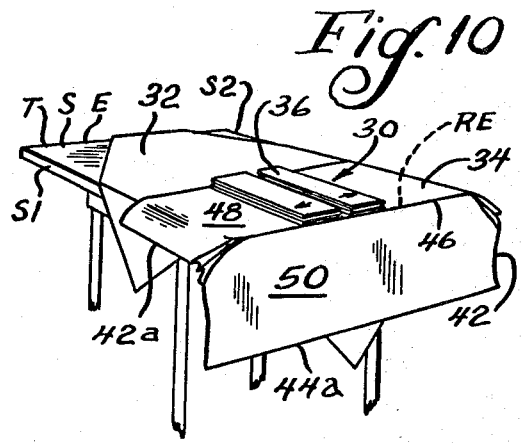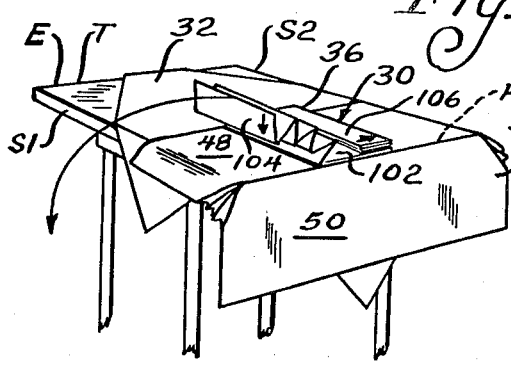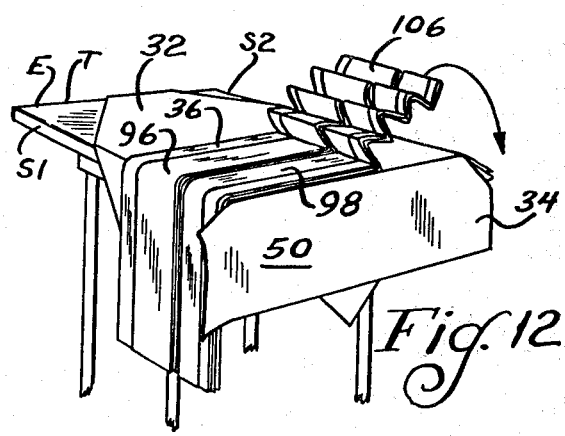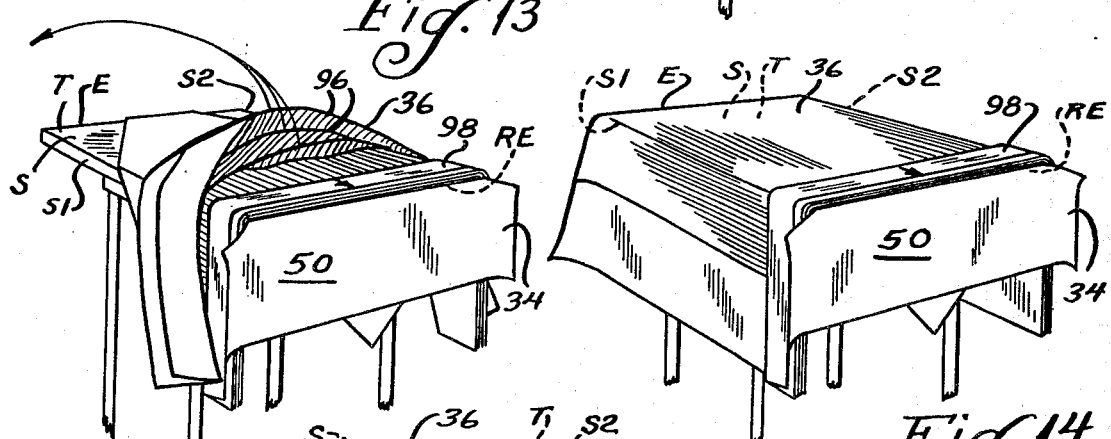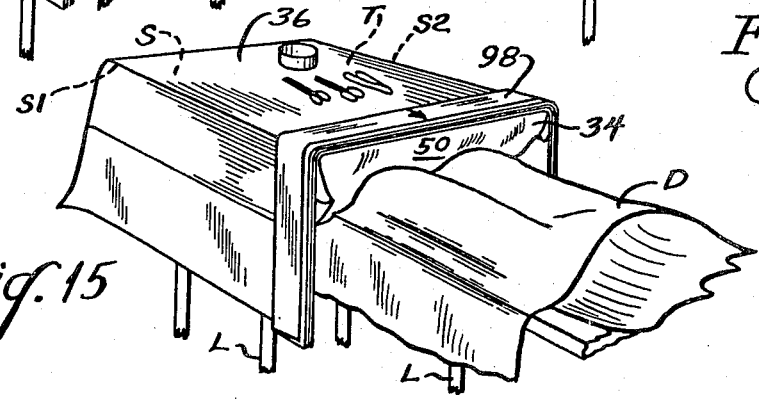

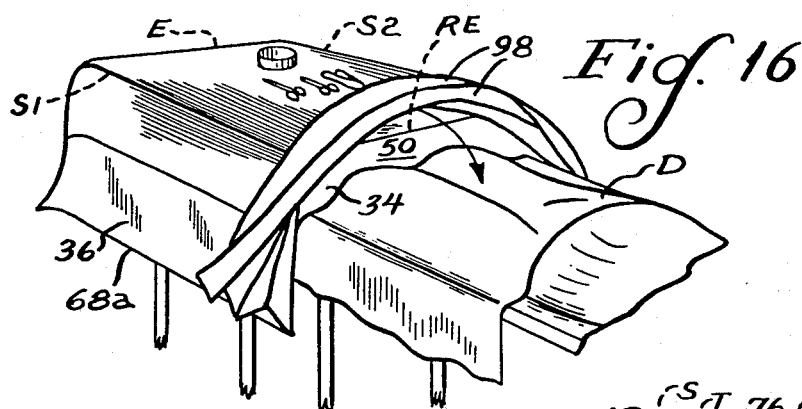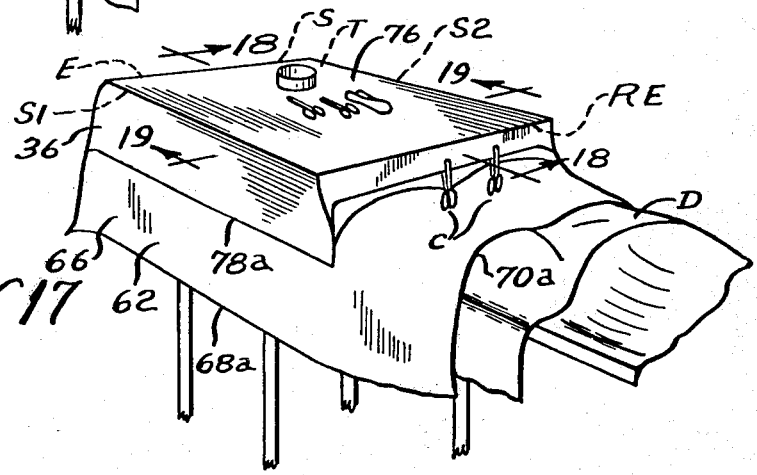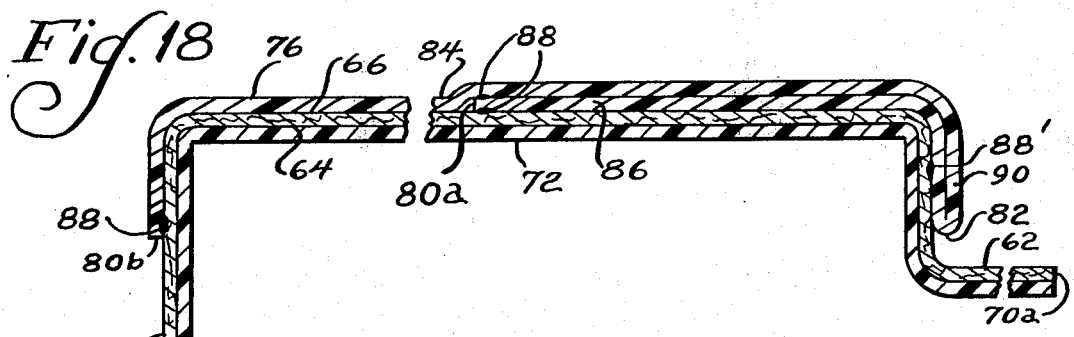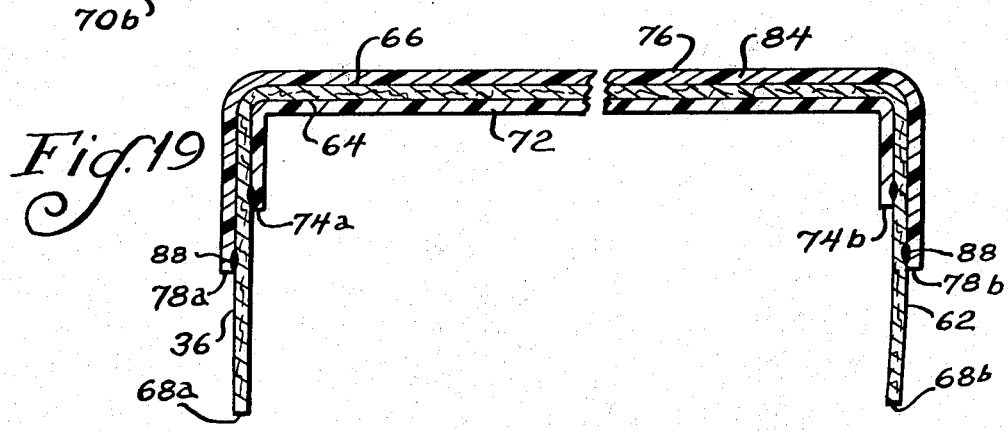

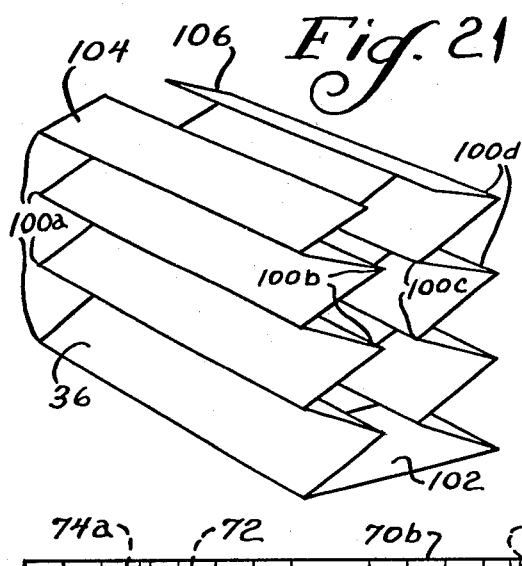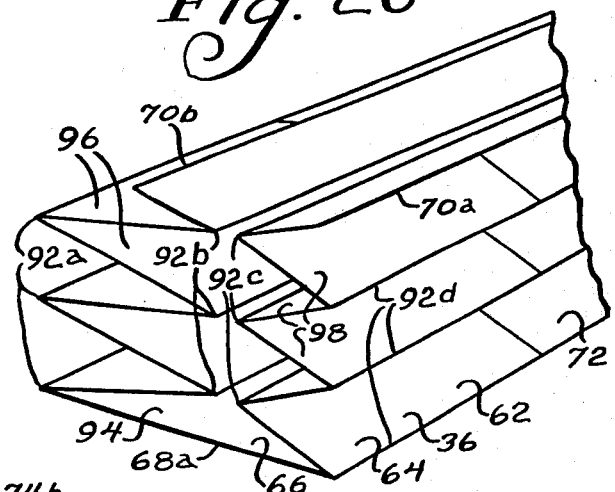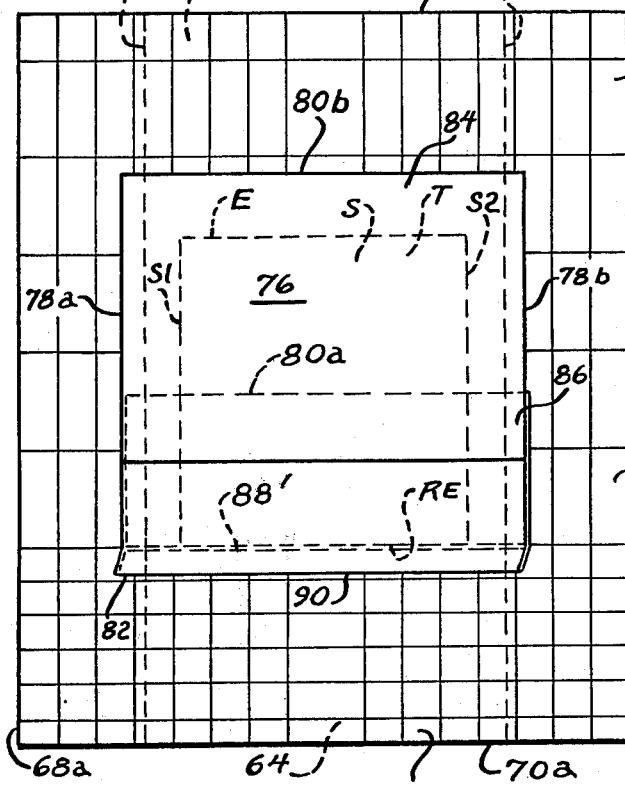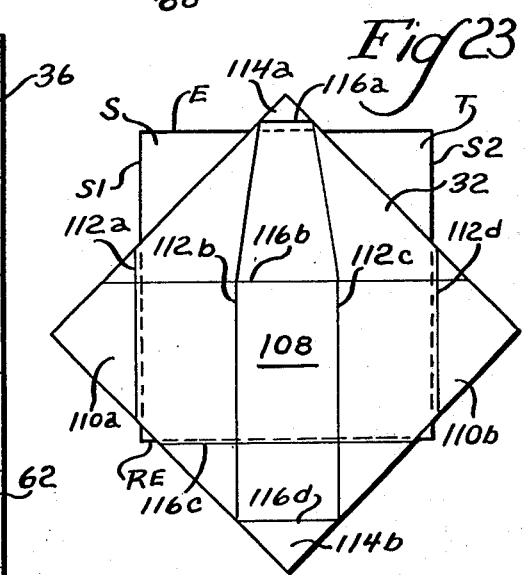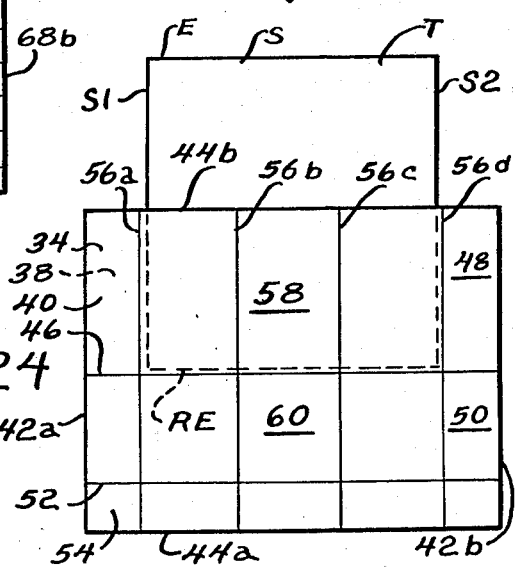

TABLE DRAPE ASSEMBLY AND METHOD

BACKGROUND OF THE INVENTION

The present invention relates to drapes, and more particularly to drapes for surgical equipment tables.

Tables are commonly used in the operating room to hold sterile articles, such as surgical instruments, during an operation. Such instrument tables are often constructed with a metal top or slab having a plurality of widely-spaced depending legs, and are arranged to modify the elevation of the table top in order that the table may be positioned over a patient with the patient being located between the spaced legs.

Since the table is non-sterile, it is necessary to cover the table with a sterile barrier prior to placement of the sterile articles on the table. However, such tables are relatively large, and are notoriously difficult to cover, particularly in a manner maintaining sterility of the covering sheets. Prior drapes or sheets used for this purpose have been difficult to place, causing inconvenience and delays to the operating room team. Moreover, even if previously sterile, the placed drape may become contaminated while the table is positioned over the patient, and during the operation the instruments and the relatively sharp corners of the metal table top abrade the drape, resulting in punctures through the drape and loss of the required sterile barrier.

SUMMARY OF THE INVENTION

A principal feature of the present invention is the provision of a drape assembly for covering a surgical equipment table in an aseptic and simplified manner.

The drape assembly of the present invention has a folded sterile set-up drape and a folded sterile table drape. The table drape has a sheet of fluid impervious material on its undersurface which has a sufficient size to cover the table. The table drape also has a protective sheet of liquid and abrasion resistant material on its upper surface which has a sufficient size to cover the table. In a preferred form, the protective sheet has a double portion for placement over a reference end edge of the table, with the doubled portion defining a laterally extending free panel adjacent an outer edge of the doubled portion. The folded drape assembly is positioned adjacent the table reference edge generally centrally between opposed side edges of the table.

A feature of the present invention is that side portions of the set-up drape may be aseptically unfolded from the assembly into a configuration extending past the side edges of the table.

Another feature of the invention is that a barrier panel of the set-up drape may be aseptically unfolded from the assembly into a configuration extending a substantial distance below the table reference edge.

Thus, a feature of the invention is that the unfolded set-up drape covers the reference table edge and provides a sterile barrier which prevents contamination to sterile operating room personnel by the table edge while placing the table drape.

Another feature of the invention is that side portions of the table drape may be aseptically unfolded from the assembly into a configuration extending a substantial distance below the table side edges.

A further feature of the invention is that a first end portion of the table drape may be aseptically unfolded from the assembly into a configuration extending a substantial distance below an end edge of the table remote the reference edge.

A feature of the invention is that a portion of the unfolded table drape covers and forms a sterile barrier over a substantial portion of the table remote the reference edge.

Still another feature of the invention is that sterile articles may be placed on the unfolded sterile drape portion covering the table preparatory to a surgical procedure or operation on a patient.

Yet another feature of the invention is that the barrier panel maintains a sterile barrier adjacent the reference table edge during placement of the sterile articles and handling of the table.

A feature of the invention is that a second end portion of the table drape may be aseptically unfolded from the assembly into a configuration covering the barrier panel of the set-up drape after the article-containing table has been positioned over the patient.

Another feature of the invention is that the unfolded second end portion of the table drape provides a sterile barrier over the lower part of the set-up drape which may become contaminated by the patient or operating room table during positioning of the table.

Thus, a feature of the invention is that the drape assembly may be placed over the table in an aseptic and simplified manner.

Yet another feature of the invention is that the fluid impervious and protective sheets prevent passage of liquid through the table drape during the surgical procedure or operation.

Still another feature of the invention is that the protective sheet prevents punctures in the table drape by sharp table edges or surgical instruments, and thus prevents loss of the sterile barrier over the table under normal usage.

A feature of the invention is that the free panel of the protective sheet provides a convenient medium for clipping and retaining articles during the surgical procedure.

Another feature of the invention is the provision of a method for placing a folded drape assembly and the table drape over an equipment table in an aseptic and simplified manner.

Yet another feature of the invention is the provision of a method for folding the drape assembly of the present invention.

Further features will become more fully apparent in the following description of the embodiments of this invention and from the appended claims.

DESCRIPTION OF THE DRAWINGS

In the drawings:

FIGS. 1–17 are perspective views illustrating steps during placement of a folded drape assembly of the present invention on an equipment table according to methods of the present invention;

FIG. 18 is a fragmentary sectional view of a table drape in the assembly taken substantially as indicated along the line 18—18 of FIG. 17;

FIG. 19 is a fragmentary sectional view of the table drape taken substantially as indicated along the line 19—19 of FIG. 17;

FIG. 20 is a fragmentary perspective view illustrating the manner in which the table drape is laterally fan folded;

FIG. 21 is a perspective view illustrating the manner in which the laterally folded table drape is transversely fan folded;

FIG. 22 is a plan view of the table drape of the present invention;

FIG. 23 is a plan view of a cover sheet for the drape assembly of the present invention; and FIG. 24 is a plan view of a set-up drape for the drape assembly of the present invention.

DESCRIPTION OF THE PREFERRED EMBODIMENTS

Referring now to FIG. 1, there is shown a foled drape assembly generally designated 30 as positioned on a surgical equipment table T, such as an equipment table sold by Phelan Manufacturing Corporation commonly used in an operating room to hold surgical instruments or other sterile articles during a surgical procedure or operation. A table of this type has a metal top or slab S, and a plurality of widely spaced depending legs L for supporting the table slab S. The elevation of the table slab S may be adjusted by suitable means (not shown) in order that the table may be positioned over a patient with the patient located intermediate the legs L to place the instruments and articles at a convenient location for use during the operation. The metal table slab S has a plurality of edges and relatively sharp corners at the juncture of the edges. For convenience in discussion only, two opposed edges of the table will be termed end edges, and the other opposed edges will be termed side edges, with a reference end edge being designated RE, an end edge remote the reference edge RE being designated E, and the side edges connecting the reference and remote edges RE and E being designated S1 and S2.

As illustrated in FIGS. 1 and 23, the folded drape assembly 30 has an outer cover sheet 32 which is made of a material resistant to passage of bacteria, such as a cellulosic or nonwoven material. As illustrated in FIGS. 6 and 24, the folded drape assembly 30 has a sterile set-up drape 34 which is also made of a material resistant to passage of bacteria, such as a cellulosic or nonwoven material. As shown in FIGS. 10 and 22, the folded drape assembly 30 further has a sterile table drape 36.

Referring to FIG. 24, the set-up drape 34 has a first surface 38 facing the table T when the set-up drape is placed, a second surface 40 facing away from the table T when the drape is placed, a pair of side edges 42a and 42b, and a pair of end edges 44a and 44b connecting the side edges 42a and b. The set-up drape 34 has a lateral fold line 46 defining a retaining panel 48 and a barrier panel 50, with the retaining panel 48 being defined by the fold line 46, the side edges 42a and b, and the end edge 44b, and with the barrier panel 50 being defined by the fold line 46, the side edges 42a and b, and the end edge 44a. As shown, the barrier panel 50 has a lateral fold line 52 extending between the side edges 42a and b and defining a laterally extending grasping panel 54. The set-up drape 34 also has a plurality of transverse fold lines 56a, 56b, 56c, and 56d defining a plurality of transverse sections, including a lateral central section 58 in the retaining panel 48, a lateral central section 60 in the barrier panel 50, and a plurality of sections intermediate the central sections 58 and 60 and the side edges 42a and 42b of the set-up drape or sheet.

Referring to FIGS. 17-19, and 22, the table drape 36 has a main sheet 62 which is made of a material resistant to passage of bacteria, such as a nonwoven material which is preferably treated to provide for liquid repellency. The main sheet 62 has a first surface 64 facing toward the table T when the table drape is placed, a second surface 66 facing away from the table T when the table drape is placed, a pair of side edges 68a and 68b, and a pair of end edges 70a and 70b connecting the side edges 68a and b.

As illustrated in FIGS. 18, 19, and 22, the table drape 36 has a sheet 72 of liquid impervious material, such as polyethylene, extending between the end edges 70a and b of the main sheet 62. As shown in FIGS. 19 and 22, the liquid impervious sheet 72 has a pair of side edges 74a and 74b spaced from the side edges 68a and 68b of the main sheet 62, with the width of the liquid impervious sheet 72 between its side edges 74a and b being sufficient to extend past the side edges of the table T when the table drape is properly placed on the table. The liquid impervious sheet 72 is secured to the first surface 64 of the main sheet 62 and defines the undersurface of the table drape when the unfolded table drape is placed on the table.

Referring to FIGS. 17-19, and 22, the table drape 36 also has a protective sheet 76 which is made of a material resistant to abrasion and passage of liquid, such as Tyvek, a trademark of E. I. duPont de Nemours. The protective sheet 76 has a pair of side edges 78a and 78b, and a pair of end edges 80a and 80b connecting the side edges 78a and b, with the width between the side edges 78a and b of the protective sheet 76 being sufficient for the protective sheet to extend past the side edges of the table T when the unfolded drape is placed on the table. As shown in FIGS. 18 and 22, the protective sheet 76 has a fold line 82 defining a cover section 84 extending between the fold line 82 and the end edge 80b, and an end section 86 extending between the fold line 82 and the end edge 80a, such that the end section 86 is folded beneath the cover section 84 to form a doubled end portion of the protective sheet 76. The protective sheet 76 is secured to the second surface 66 of the main sheet 62 in this configuration by suitable means, such as by lines of adhesive 88, including a line of adhesive 88' which is spaced slightly from the fold line 82 of the protective sheet 76. Thus, the doubled protective sheet 76 defines an upper surface of the table drape 36 when the unfolded drape is placed on the table, with the length of the cover sheet 84 between the fold line 82 and the end edge 80b being sufficient to extend past the end edges of the table T. Also the line of adhesive 88' defines a free clip panel 90 of doubled material adjacent the fold line 82 for a purpose which will be described below.

Referring to FIG. 20, the table drape 36 has a plurality of lateral fold lines 92a, 92b, 92c, and 92d extending between the side edges of the main sheet 62, with the fold lines 92a and 92d defining a laterally extending central panel 94, with the fold lines 92a and 92b defining a first set of lateral fan or accordion folds 96, and with the fold lines 92c and 92d defining a second set of lateral fan or accordion folds 98. As shown, the first and second sets of lateral fan folds 96 and 98, respectively, are folded over the second surface 66 of the central panel 94, with the distance between the fold lines 92a and 92b in the first set of fan folds 96 being greater than the distance between the fold lines 92c and 92d in the second set of fan folds 98 to provide additional material in the first set of fan folds 96 for a purpose which will be described below. In the laterally folded configuration, the fold lines 92b and 92c of the lateral fan folds define inner edges of the fan folds which abut each other in the drape, and the fold lines 92a and 92d define outer edges of the first and second sets of fan folds. Also, the sets of fan folds 96 and 98 have laterally extending panels at their outer ends adjacent the end edges 70b and 70a which are convenient for grasping during placement of the table drape.

Referring to FIG. 21, the laterally folded table drape 36 has a plurality of transverse fold lines 100a, 100b, 100c, and 100d defining a transverse central panel 102, a first set of transverse fan folds 104, and a second set of transverse fan folds 106, with the first and second sets of transverse fan folds 104 and 106, respectively, being folded over the outer ends of the lateral fan folds in the transverse central panel 102. In this configuration, the outer ends of the transverse fan folds 104 and 106 define transverse panels for convenient grasping during placement of the drape.

With reference to FIG. 24, the transversely folded table drape is positioned on the central section 58 of the set-up drape retaining panel 48 with the outer ends of the transverse fan folds facing away from the second surface 40 of the set-up drape 34. Next, the barrier panel 50 is folded over the table drape along the fold line 46, and the grasping panel 54 is folded back along the fold line 52. Finally, the side sections of the set-up drape defined by the transverse fold lines 56a, b, c, and d are folded over the central section 60 of the barrier panel 50 to cover the folded table drape with the folded set-up drape.

With reference to FIG. 23, the folded table and set-up drapes are positioned on a central section 108 of the cover sheet 32, side portions 110a and 110b of the cover sheet 32 are folded inwardly along transverse fold lines 112a, 112b, 112c, and 112d, after which end portions 114a and 114b of the cover sheet 32 are folded inwardly along lateral fold lines 116a, 116b, 116c, and 116d. In this manner, the folded set-up drape is covered by the cover sheet.

Referring again to FIG. 1, the use of the folded drape assembly 30 according to a method of the present invention is described as follows. Initially, the folded drape assembly is retained in a package (not shown) of a material resistant to passage of bacteria, such as polyethylene, and the drape assembly is sterilized within the package. When ready for use, the protective package is opened by a non-sterile person in the operating room, such as a circulating nurse, who removes the drape assembly 30 from the package while grasping the cover sheet 32 which permits handling of the drape assembly by non-sterile hands without contamination of the covered set-up and table drapes. The circulating nurse places the folded drape assembly on the table top or slab S with a designated edge of the drape assembly aligned with the reference edge RE and with the assembly located generally centrally between the side edges S1 and S2 of the table T. The proper placement for the edge of the drape assembly is indicated by the indicia or printed arrow on the outside of the cover sheet 32, as shown. As will be seen below, in this reference position of the assembly, the fold line 46 of the set-up drape 34 (FIG. 24) and the outer edges of the second set of lateral fan folds 98 defined by fold lines 92d (FIG. 20) are located adjacent the reference edge RE of the table.

Referring to FIG. 1, the circulating nurse grasps the end portion 114a of the cover sheet 32, and, as shown in FIG. 2, unfolds the end portion 114a of the cover sheet 32 towards the remote edge E of the table T.

Next, with reference to FIGS. 2 and 3, the circulating nurse grasps the side portion 110a of the cover sheet 32, and unfolds the side portion toward the side edge S1 of the table T. As illustrated in FIGS. 3 and 4, the circulating nurse then grasps the other side portion 110b of the cover sheet 32, and unfolds this side portion toward the side edge S2 of the table. Finally, as illustrated in FIGS. 4 and 5, the circulating nurse grasps the other end portion 114b of the cover sheet 32, and unfolds the end portion 114b over the reference edge RE, after which the end portion 114b of the cover sheet 32 depends below the reference edge RE, as shown in FIG. 6. (The configuration of the unfolded cover sheet 32 relative the table size is illustrated in FIG. 23.) Thus, the folded set-up drape 34 has been exposed adjacent the reference edge RE of the table T without contamination of the set-up drape by the non-sterile hands of the circulating nurse.

At this time, a sterile person in the operating room, such as a scrub nurse, unfolds the sterile set-up drape 34 in the following manner. With reference to FIGS. 6 and 7, the scrub nurse grasps the grasping panel 54 in one side portion of the set-up drape 34, and unfolds the side portion toward the side edge S1 of the table, after which she grasps the grasping panel 54 in the other side portion of the set-up drape 34 and unfolds it toward the other side edge S2 of the table T, as shown in FIGS. 7 and 8. Next, as illustrated in FIGS. 8 and 9, the scrub nurse grasps the grasping panel 54 in the central section 60 of the barrier panel 50, and unfolds the barrier panel 50 from the drape assembly 30 into a configuration with the barrier panel 50 extending a substantial distance below the reference edge RE of the table T, as shown in FIG. 10. (The configuration of the unfolded set-up drape 34 relative the table size is illustrated in FIG. 24.) With reference to FIG. 10, the set-up drape 34 has a sufficient width between the side edges 42a and b to extend past the side edges S1 and S2 of the table T, such that the unfolded set-up drape 34 covers the entire reference edge RE of the table including the corners of the table at the juncture of the side edges S1 and S2 and the reference edge RE. Thus, the unfolded set-up drape 34 exposes the table drape 36 without contamination of the table drape, and the unfolded set-up drape 34 forms a sterile barrier along the reference edge RE of the table to prevent contamination of the sterile nurse by the non-sterile table during placement of the table drape 36. The weight of the table drape 36 on the retaining panel 48 of the set-up drape 34 retains the set-up drape at its barrier position.

The sterile table drape 36 is unfolded by the sterile scrub nurse in the following manner. First, with reference to FIGS. 10 and 11, the transverse fan folds 104 are unfolded from the assembly 30 into a configuration with side portions of the table drape extending past the side edge S1 of the table, after which the transverse fan folds 106 of the table drape are unfolded from the assembly 30 into a configuration with side portions extending past the side edge S2 of the table T, as shown in FIGS. 12 and 13, such that the side portions of the partially unfolded table drape 36 extend a substantial distance below the respective side edges S1 and S2 of the table. Next, as illustrated in FIG. 13, the set of lateral fan folds 96 of the table drape 36 are unfolded toward the remote edge E of the table T, such that an end portion of the table drape is unfolded from the assembly into a configuration extending a substantial distance below the remote table edge E, as best shown in FIG. 14. In this configuration, the partially unfolded table drape 36 provides a sterile barrier for the table around its edges S1, E, and S2, while the barrier panel 50 of the set-up drape 34 continuously provides a sterile barrier along the table reference edge RE. The second set of fan folds 98 of the table drape 36 remains in a folded configuration for later use, as described below.

At this time, sterile articles, such as surgical instruments, are placed on the unfolded portion of the table drape 36 covering the table top S, and the patient is prepared for the operation, including placement of a drape on the patient in a separate draping procedure. As before, the barrier panel 50 of the set-up drape 34 provides a sterile barrier for the reference edge RE of the table during placement of instruments on the table drape 36 and while moving the table. When the patient has been properly prepared for the operation, the table T may be positioned over the patient, e.g., his legs, with the patient located intermediate the legs L of the table T, as shown in FIG. 15. Since the barrier panel 50 of the set-up drape 34 passes over the patient's feet, the barrier panel 50 may become contaminated by the patient or by the operating room table as the table is being positioned over the patient. However, as illustrated in FIG. 16, the second set of lateral fan folds 98 may be unfolded by the sterile scrub nurse into a configuration over the barrier panel 50 of the set-up drape 34, such that the unfolded second set of lateral fan folds forms a continuous sterile barrier with a sterile drape D previously placed over the patient, as illustrated in FIG. 17. At this time, the table has been positioned near the surgical site for convenient use of the surgical instruments on the sterile table drape, and the unfolded table drape 36 provides a sterile barrier completely around the sides of the table, including the reference edge RE which is positioned adjacent the surgical site.

Thus, in accordance with the present invention, the cover sheet permits handling of the folded drape assembly by non-sterile hands, and the folded assembly is positioned adjacent a reference edge of the instrument table. The unfolded barrier panel of the sterile set-up drape provides a sterile barrier for the reference edge of the table while the table drape is partially unfolded to cover a substantial portion of the table and while articles are placed on the table. After the instruments have been placed on the table, the table is positioned over the patient and the remaining portion of the table drape is unfolded to provide a sterile barrier over the lower part of the set-up drape. Thus, the drape assembly of the present invention permits the table to be covered in an aseptic and simplified manner according to the method of draping the table of the present invention.

The configuration of the unfolded table drape 36 relative the table size is illustrated in FIG. 22. As shown, the protective sheet 76 of the placed table drape 36 extends past the edges S1, E, S2, and RE of the table. The durable material of the protective sheet 76 prevents puncturing of the table drape 36 by sharp corners of the table at the juncture of the table side and end edges, and provides a cushion for the instruments which are dropped onto the table during the operation to prevent puncturing of the table drape 36 by the instruments. The portion of the unfolded table drape located over the table top S adjacent the reference edge RE is subject to the most abuse during the operation, since the reference edge RE of the table is located nearest the surgical site. Consequently, instruments are repeatedly dropped upon and removed from this portion of the table, and operating room personnel brush against and apply pressure to this part of the drape. The doubled portion of the protective sheet 76 provides additional resistance against abrasion of the drape by the instruments and pressure exerted against the table corners to prevent puncturing of the table drape 36 which otherwise would result in loss of the sterile barrier over the table.

With reference to FIGS. 17, 18, and 22, the clip panel 90 of the protective sheet 76 is located slightly below the reference edge RE of the table T when the unfolded table drape 36 has been properly placed on the table T. Thus, the clip panel 90 provides a convenient medium on which clips C, such as towel clips, may be attached during the operation, and provides a strong segment of the drape on which other items, such as aspiration tubing, cautery cord, etc., may be attached in a convenient manner. Since both opposed surfaces of the clip panel 90 are sterile, the sterile barrier over the table is not lost when the clips should puncture the clip panel 90.

With reference to FIGS. 17–19, and 22, the protective sheet 76 is resistant to passage of liquid, and the liquid impervious sheet 72 and the protective sheet 76 provide a barrier to prevent passage of liquid through the table drape 36 during the operation, which otherwise might result in loss of the sterile barrier.

According to a method of the present invention, the table is covered by covering a reference edge of the table with a first sterile sheet section in a configuration extending below the reference edge of the table. A substantial portion of the table including an edge remote the reference edge is covered with a second sterile sheet section, and the first sheet section below the reference edge is covered with a third sterile sheet section.

According to another method of the present invention, a folded drape assembly is positioned adjacent a reference edge of the table. Side portions of a sterile set-up drape are unfolded from the assembly into a configuration extending past opposed edges of the table adjacent the reference edge. A barrier panel of the set-up drape is unfolded from the assembly over the reference edge into a configuration extending a substantial distance below the reference edge with the set-up drape covering the reference edge and corners of the table at the juncture of the opposed table edges and reference edge. Side portions of a sterile table drape are unfolded from the assembly into a configuration with the side portions extending a substantial distance below the opposed edges of the table. A first end portion of the table drape is unfolded from the assembly into a configuration extending a substantial distance below an edge of the table remote the reference edge. A second end portion of the table drape is unfolded from the assembly into a configuration covering the barrier panel below the table reference edge.

The table is covered with the table drape according to a method of the present invention. The folded sterile table drape is positioned adjacent the reference edge of the table, and side portions of the drape are unfolded to a location extending substantially below the opposed edges of the table adjacent the reference edge. A first end portion of the drape is unfolded to a location extending substantially below an edge of the table remote the reference edge, the table is positioned with the reference edge located adjacent the patient, and a second end portion of the drape is unfolded to a location below the reference table edge.

The drape assembly is also folded according to a method of the present invention. A table drape is folded along a plurality of lateral fold lines defining a pair of laterally stacked fan folds, and the laterally folded drape is folded along a plurality of transverse fold lines defining a pair of transversely stacked fan folds. The transversely folded drape is positioned on a lateral central portion of a set-up drape, and an end section of the set-up drape is folded over the folded table drape. Lateral side portions of the set-up drape are folded over the transverse fan folds of the table drape.

The foregoing detailed description is given for clearness of understanding only, and no unnecessary limitations should be understood therefrom, as modifications will be obvious to those skilled in the art.

I claim:

1. A drape assembly for a surgical equipment table comprising, first sterile sheet means of a material resistant to passage of bacteria and folded into said assembly, second and third sterile sheet means of a material resistant to passage of bacteria and resistant to abrasion and passage of liquid in at least a portion thereof, said second and third sheet means being folded into said assembly together with said first sheet means, said first sheet means being unfoldable from said assembly into a configuration over and depending below a reference edge of the table while the second and third sheet means remain in a folded configuration to provide a sterile barrier over the reference edge, said second sheet means being unfoldable from the assembly into a configuration covering a portion of the table and an edge of the table remote the reference edge while the third sheet means remains in a folded configuration to permit placement of sterile articles on the sterile second sheet means, said third sheet means being unfoldable from the assembly into a configuration over the first sheet means to provide a sterile barrier over the first sheet means.

2. A drape assembly for a surgical equipment table, comprising:
a set-up drape comprising a sterile barrier sheet of a material resistant to passage of bacteria and folded into the assembly, said barrier sheet including a barrier panel unfoldable from the assembly into a configuration covering and depending below a reference edge of the table; and
a sterile table drape folded into said assembly and having a first folded section being unfoldable from the assembly into a configuration covering a remote portion of the table relative said reference edge, and a second folded section being unfoldable from the assembly into a configuration covering said barrier panel.

3. The assembly of claim 2 wherein said table drape includes a section of liquid impervious material on a surface of the unfolded drape facing the table and having sufficient dimensions to cover the table.

4. The assembly of claim 2 wherein said table drape includes a protective sheet of a material resistant to abrasion on a surface of the unfolded drape facing away from the table, said protective sheet having sufficient dimensions to at least substantially cover the table and to overlie the table reference edge and corners of the reference edge.

5. The assembly of claim 4 wherein said protective sheet includes a doubled portion overlying the table reference edge and corners in the unfolded drape.

6. The assembly of claim 5 wherein said doubled portion has a free segment adjacent an edge of the doubled portion and extending beyond the table reference edge in the unfolded drape.

7. The assembly of claim 2 including a cover sheet of a material resistant to passage of bacteria folded over and covering the set-up and table drapes to permit aseptic handling thereof.

8. The assembly of claim 2 wherein the table drape includes third and fourth sections, said sections being unfoldable from the assembly into a configuration covering opposed edges of the table adjacent the table reference edge.

9. A drape assembly for a surgical equipment table having a pair of opposed edges and a pair of edges connecting the opposed edges, comprising:
a sterile table drape having a sufficient width to extend past the opposed edges of the table and being resistant to passage of liquid and bacteria, said table drape having first and second sets of lateral fan folds with the length of the drape in the first set of fan folds being sufficient to extend past a connecting edge of the table remote a reference connecting edge of the table when the assembly is placed in a reference position with an outer edge of the second set of fan folds being positioned adjacent the reference table edge, said table drape having a first and second set of transverse fan folds of the laterally folded drape for covering portions of the table adjacent the opposed edges when unfolded from the drape in the reference position; and
a sterile set-up drape of a material resistant to passage of bacteria, said set-up drape being folded around the folded table drape and having a barrier panel being unfoldable from the assembly in said reference position into a configuration extending below the table reference edge and with side portions of the set-up drape extending past corners of the reference edge.

10. The assembly of claim 9 wherein said set-up drape includes a retaining panel extending from said barrier panel, in which said transversely folded table drape is positioned on a lateral central portion of said retaining panel with outer portions of the transverse fan folds in the folded table drape facing away from the retaining panel, said barrier panel is folded over the outer ends of the transverse fan folds, and in which lateral side portions of the set-up drape are folded over a lateral central portion of the folded over barrier panel.

11. The assembly of claim 9 wherein the distance between adjacent fold lines defining the first lateral set of fan folds is greater than the distance between adjacent fold lines defining the second lateral set of fan folds.

12. The assembly of claim 9 including a cover sheet of a material resistant to passage of bacteria, said cover sheet being folded around and covering the folded set-up drape.

13. A drape assembly for a surgical equipment table, comprising:
a sterile table drape for covering the table, said table drape being folded into a configuration of reduced dimensions defining an edge for placement adjacent a reference edge of the table in a reference position of the assembly; and a set-up drape of a material resistant to passage of bacteria, said set-up drape having a fold line defining a retaining panel and a barrier panel, said table drape being positioned on a lateral central portion of the retaining panel with said edge of the folded table drape being positioned adjacent said fold line of the set-up drape, and said barrier panel being positioned over the folded table drape, with lateral side portions of the set-up drape being folded over a lateral central portion of the barrier panel.

14. The assembly of claim 13 wherein said barrier panel includes a lateral fold line defining a folded back grasping panel.

15. A drape assembly for a surgical equipment table having a pair of side edges and a pair of end edges, comprising:

a sterile table drape having a pair of side edges, a pair of end edges connecting the side edges, a first surface for facing the table when the table drape is placed on the table, and a second surface facing away from the table when the table drape is placed on the table, said table drape having a sufficient width between said drape side edges to extend a substantial distance beyond the side edges of the table, and having a sufficient length between said drape end edges to extend a substantial distance beyond said table end edges, said table drape having a lateral central panel extending between the drape side edges and a plurality of lateral fold lines extending between the drape side edges, said lateral fold lines defining first and second sets of lateral fan folds overlying the second panel and having inner and outer edges, said first set of lateral fan folds having a sufficient length between the lateral central panel and the associated drape end edge to extend a substantial distance beyond a table end edge remote a reference table end edge when the outer edge of the second set of lateral fan folds is placed adjacent the reference table end edge in a reference position of the assembly, said second set of lateral fan folds having a sufficient length between the lateral central panel and the associated drape end edge to extend a substantial distance beyond the table reference edge when unfolded from said reference position, and the laterally folded drape having a transverse central panel for placement generally centrally relative the table side edges in said reference position and a plurality of transverse fold lines defining first and second sets of transverse fan folds positioned over an outer surface of the lateral fan folds in the transverse central panel and having inner and outer edges; and a sterile set-up drape of a material resistant to passage of bacteria, said set-up drape having a pair of side edges, a pair of end edges connecting the side edges, a first surface for facing the table, and a second surface for facing away from the table, with said set-up drape having a sufficient width between said side edges to extend past the table side edges, said set-up drape having a lateral reference fold line extending between the side edges of the set-up drape and defining a retaining panel and a barrier panel, with said barrier panel having a sufficient length between said reference fold line and the associated end edge of the set-up drape to extend a substantial distance beyond the table reference edge when the barrier panel is unfolded from the assembly with the reference fold line positioned adjacent the table reference edge in the reference position of said assembly, said transversely folded table drape being positioned on the second surface of said retaining panel at a lateral central location between the side edges of the set-up drape with the outer edge of said second lateral fan folds located adjacent the reference fold line of the set-up drape, said barrier panel being folded over the outer ends of the transverse fan folds and having a lateral fold line defining a folded back grasping panel, said laterally folded set-up drape having transverse fold lines defining transverse sections folded over a lateral central section of said barrier panel.

16. A table drape for a surgical equipment table having a pair of opposed edges and a pair of edges connecting the opposed edges comprising, a main sterile sheet of a material resistant to passage of bacteria and having sufficient dimensions to extend a substantial distance beyond the opposed and connecting edges of the table, and a sterile protective sheet of a liquid and abrasion resistant material, said protective sheet being attached to the main sheet and having a sufficient width and length to extend past the opposed and connecting edges of the table, said protective sheet having a clip panel being at least partially free of attachment from the main sheet and defining at least a portion of an outer edge of the protective sheet.

17. The drape of claim 16 including a fluid impervious sheet secured to an opposed surface of the main sheet relative the protective sheet and having sufficient dimensions to cover the table.

18. A table drape for a surgical equipment table having a pair of side edges and a pair of end edges comprising, a main sterile sheet of a material resistant to passage of bacteria and having a pair of side edges and a pair of end edges connecting the side edges, said main sheet having a sufficient width between the sheet side edges to extend a substantial distance beyond the table side edges when the drape is placed on the table, and a sufficient length between the sheet end edges to extend a substantial distance beyond the table end edges when the drape is placed, and a protective sheet of liquid and abrasion resistant material having a pair of side edges and a pair of end edges connecting the side edges, said protective sheet being secured to the main sheet with the side edges of the protective sheet being generally centrally located between the side edges of the main sheet, said protective sheet having a sufficient width between its side edges to extend past the side edges of the table when the drape is placed, and having a lateral fold line extending between the side edges of the protective sheet defining an end section extending between said fold line and one end edge of the protective sheet and defining a cover section extending between said fold line and the other end edge of the protective sheet, said end section being folded under the cover section and secured between said cover section and the main sheet with said cover and end sections defining a laterally extending free clip panel of doubled material adjacent the fold line, said cover section having a sufficient length between said fold line and said other end edge of the protective sheet to at least substantially cover the table when the drape is placed on the table with the clip panel located adjacent an end edge of the table.

19. A method of covering a table in an aseptic manner, comprising the steps of:
covering a reference edge of the table with a first sterile sheet section in a configuration extending below the reference edge;
covering a substantial portion of the table including an edge remote the reference edge with a second sterile sheet section; and
covering the first sheet section below the reference edge with a third sterile sheet section.

20. A method of covering a table in an aseptic manner, comprising the steps of:
positioning a folded drape assembly adjacent a reference edge of the table;
unfolding side portions of a sterile set-up drape from the assembly into a configuration extending past opposed edges of the table adjacent the reference edge;
unfolding a barrier panel of the set-up drape from the assembly over the reference edge into a configuration extending a substantial distance below the reference edge with the set-up drape covering the reference edge and corners of the table at the juncture of said opposed table edges and reference edge;
unfolding side portions of a sterile table drape from the assembly into a configuration with the side portions extending a substantial distance below said opposed edges of the table;
unfolding a first end portion of the table drape from the assembly into a configuration extending a substantial distance below an edge of the table remote the reference edge; and
unfolding a second end portion of the table drape from the assembly into a configuration covering the barrier panel below the table reference edge.

21. The method of claim 20 including the step of unfolding a cover sheet from the assembly between said positioning and first unfolding steps.

22. The method of claim 20 including the step of positioning the table reference edge adjacent a patient between the last two unfolding steps.

23. A method of covering a surgical equipment table in an aseptic manner, comprising the steps of:
positioning a folded sterile table drape adjacent a reference edge of the table;
unfolding side portions of the drape to a location extending substantially below opposed edges of the table adjacent the reference edge;
unfolding a first end portion of the drape to a location extending substantially below an edge of the table remote the reference edge;
positioning the table with the reference edge located adjacent a patient; and
unfolding a second end portion of the drape to a location below the reference table edge.

24. A method of folding a drape assembly for a surgical equipment table, comprising the steps of:
folding a table drape along a plurality of lateral fold lines defining a pair of laterally stacked fan folds;
folding the laterally folded drape along a plurality of transverse fold lines defining a pair of transversely stacked fan folds;
positioning the transversely folded drape on a lateral central portion of a set-up drape;
folding an end section of the set-up drape over the folded table drape; and
folding lateral side portions of the set-up drape over the transverse fan folds of the table drape.

* * * * *